US007374772B2

(12) United States Patent
Bommarito

(10) Patent No.: US 7,374,772 B2
(45) Date of Patent: May 20, 2008

(54) TOPICAL ANTIFUNGAL TREATMENT

(76) Inventor: Alexander A. Bommarito, 12555 W. Freeland Rd., Freeland, MI (US) 48623

( * ) Notice: Subject to any disclaimer, the term of this patent is extended or adjusted under 35 U.S.C. 154(b) by 835 days.

(21) Appl. No.: 10/289,552

(22) Filed: Nov. 7, 2002

(65) Prior Publication Data

US 2004/0091506 A1 May 13, 2004

(51) Int. Cl.
*A01N 25/34* (2006.01)
*A61K 31/07* (2006.01)

(52) U.S. Cl. ...................... 424/404; 514/725
(58) Field of Classification Search ................ 424/401, 424/404
See application file for complete search history.

(56) References Cited

U.S. PATENT DOCUMENTS

| | | | |
|---|---|---|---|
| 4,263,313 A | 4/1981 | Eckert et al. | |
| 4,323,558 A | 4/1982 | Nelson | |
| 4,895,727 A | 1/1990 | Allen | |
| 5,209,932 A | 5/1993 | Nichols | |
| 5,482,965 A | 1/1996 | Rajadhyaksha | |
| 5,661,170 A | 8/1997 | Chodosh | |
| 5,846,971 A | 12/1998 | Sangekar et al. | |
| 6,011,067 A | 1/2000 | Hersh | |
| 6,017,520 A | 1/2000 | Synodis et al. | |
| 6,017,900 A | 1/2000 | Falk et al. | |
| 6,080,744 A | 6/2000 | Ayon-Covarrubias | |
| 6,096,338 A | 8/2000 | Lacy et al. | |
| 6,159,977 A | 12/2000 | Reeves | |
| 6,224,887 B1 | 5/2001 | Samour et al. | |
| 6,231,865 B1 * | 5/2001 | Hsu et al. | |
| 6,231,875 B1 | 5/2001 | Sun et al. | |
| 6,267,985 B1 | 7/2001 | Chen et al. | |
| 6,268,355 B1 | 7/2001 | Mizobuchi et al. | |
| 6,299,900 B1 | 10/2001 | Reed et al. | |
| 6,306,843 B1 | 10/2001 | Burghart et al. | |
| 6,492,395 B1 | 12/2002 | Scheiwe et al. | |
| 6,524,593 B1 | 2/2003 | Yu et al. | |
| 6,541,517 B1 | 4/2003 | Murphy et al. | |
| 6,762,158 B2 * | 7/2004 | Lukenbach et al. | |

OTHER PUBLICATIONS

Jorge E. Arrese, Claudine Pierard-Franchimont and Gerald E. Pierard, "A Plea to Bridge the Gap Between Antifungals and the Management of Onychomycosis" Am J Clin Derm 2001.
AHFS Drug Information 2002; 3361-3401.
M.S.P. Sastry, P. Rama Rao, and P.V. Diwan, "Percutaneous Absorption of Naproxen From Different Ointment Bases in Rats." Indian Journal of Pharmacology 1995; 27:130-132.
AHFS Drug Information 2002; 3402-3043.
Jacques F.G.M. Meis and Paul E. Verweij, "Current Management of Fungal Infections", Drugs 2001:61 Suppl. 1:13-25 (Adis International Limited).
Vijay N. Joish and Edward P. Armstrong, "Which Antifungal Agent for Onychomycosis", PharmacoEconomics 2001; 19(10): 983-1002; (Adis International Limited).
Jeffrey M. Robbins, DPM, "Recognizing, treating, and preventing common foot problems"; Cleveland Clinic Journal of Medicine, 67(1), Jan. 2000.
James W. Shaw, Vijay N. Joish and Stephen Joel Coons, "Onychomycosis Health-Related Quality of Life Considerations", PharmacoEconomics 2002:20(1): 23-36 (Adis International Limited).
Daniele Debruyne and Antoine Coquerel, "Pharmacokinetics of Antifungal Agents in Onychomycoses", Clin Pharmacokinet 2001; 40(6): 441-472 (Adis International Limited).
R.J. Hay "The future of onychomcosis therapy may involve a combination of approaches", British Journal of Dermatology (2001) 145, (Suppl. 60), 3-8.
Medlineplus Drug Information; Internet; "Tolnafte".
Fay Crawford,PhD; Philip Young, PhD, Christine Godfrey, BA; Sally E.M. Bell-Syer, MSc; Rachel Hart, BSc, Elizabeth Brunt, BMBS; Ian Russel, PhD, "Oral Treatments for Toenail Onychomycosis"; Arch Dermatology vol. 138 (Jun. 2002), p. 811-816.
Kenneth James Meehan, PA-C; Charles Miller, MD., "The clinical challenge of onychomycosis", JAAPA 14(4), Apr. 2001; p. 43-50.
Catherine M. Tom and Michael P. Kane, "Management of toenail onychomycosis", American Society of Health-System Pharmacists, vol. 56, p. 865-869; (May 1, 1999).

(Continued)

*Primary Examiner*—Humera N Sheikh
(74) *Attorney, Agent, or Firm*—Alexander D. Bommarito

(57) ABSTRACT

The present invention is a topical skin preparation for treatment of fungal infections of the skin and nails. The preparation comprises triacetin in combination with an antifungal agent. In a preferred form, the preparation further comprises, a fatty acid source such as a fish oil. In a preferred embodiment, cod liver oil and tolnaftate are used in combination with triacetin. The concentrations of these constituents are 96.0-99.0% concentration triacetin, 0.5-3.0% concentration tolnaftate and 0.5-1.0% concentration cod liver oil, in one preferred embodiment. Other compounds, such as ethyl alcohol, amino acids such as n-acetylcysteine, and herbal additives may also be added to the preparation. Further, other antifungal agents such as nystatin, clortimazole, econazole, ketoconazole, miconazole, solconazole, oxiconizole, naftifine, terbinafine, and butenafine, for example, may be substituted for the antifungal agent tolnaftate. The preparation of the present invention is effective in treating immune compromised patients and those with diabetes, as well as relatively healthy persons.

26 Claims, No Drawings

OTHER PUBLICATIONS

Aditya Kumar Gupta and Stephanie Humke, "The prevalence and management of onychomycosis in diabetic patients", EJD 5(10):379-384 (Jul.-Aug. 2000).

Phillip Rodgers, M.D.and Mary Bassler, M.D., "Treating Onychomycosis" American Family Physician 63(4); p. 663-672 (Feb. 15, 2001).

Aditya K. Gupta and Neil H. Shear, "A Risk-Benefit Assessment of the Newer Oral Antifungal Agents Used to Treat Onychomycosis", Drug Safety Jan. 2000: 22(1); 33-52 (Adis International Limited).

E.G.V: Evans, "The rational for combination therapy", British Journal Of Dermatology (2001) 145. (Suppl.60). 9-13.

Handbook Of Nonprescription Dugs, 11th Edition; American Pharmaceutical Association (p. 558-562).

The Merck Manual, Sixteenth Edition (p. 2419-2422).

Philip Fleckman, MD, Emily F. Omura, MD., "Histopathology of the Nail", Advances In Dermatology, vol. 17, p. 385-406, 2001.

Mary P. English, "Nails and Fungi", British Journal of Dermatology (1976), 94, p. 697-701.

Nardo Zaias, MD, "Onychomycosis", Arch Dermatology, vol. 105, p. 263-274 (Feb. 1972).

Rudolf L. Baer, M.D., Stanley A. Rosenthal, Ph.D., "Experimental Investigations on Mechanism Producing Acute Dermatophytosis of Feet", J.A.M.A 160(3) p. 184-190, (Jan. 21, 1956).

Martindale The Extra Phamacopoeia, Thirtieth Edition; p. 332, The Pharmaceutical Press 1993.

The Merck Index, An Encyclopedia of Chemicals, Drugs, and Biologicals, Eleventh Edition; "Triacetin", Merck & Co., Inc. 1989.

The Merck Index, An Encyclopedia of Chemicals, Drugs, and Biologicals, Eleventh Edition; "Tolnaftate"; Merck & Co., Inc. 1989.

"Fungal Infections of Fingernails and Toenails", American Academy of Family Physicians, Information from Your Family Doctor (Feb. 2001).

* cited by examiner

TOPICAL ANTIFUNGAL TREATMENT

FIELD OF THE INVENTION

The present invention is generally a topical skin treatment. More specifically, the present invention is a topical skin treatment effective at treating skin and nail infections such as *onychomycosis, Tinea pedis, Tinea cruris, Tinea corporis, Tinia versicolor* and *Candidiasis*, among others.

BACKGROUND OF THE INVENTION

Fungal skin infections, often called dermatomycoses, are among the most common skin infections. Characteristically, these infections exhibit single or multiple lesions that may produce a mild scaling, or deep, inflamed, nodular lesions. Many of these infections are superficial, affecting the hair, nails, and/or skin, and are generally caused by three fungi: *Trichophyton, Microsporum*, and *Epidermophyton*.

Since clinical differentiation of the similar dermaphytes is difficult, these infections are discussed or grouped and treated according to the sites involved. Diagnosis of difficult, non-responding pathogenic organisms can be identified by scraping of the developed lesions, and examining by either direct microscopic examination of a potassium hydroxide preparation or by fungal culture.

Some of the fungal skin infections are classed as follows. *Tinea Pedis* is a very common fungal infection, which is commonly known as athletes foot or ringworm of the feet. *Tinea pedis* can be difficult to cure in some affected persons.

*Tinea curis* is commonly known as jock itch, and is caused by *Epidermophyton floccosum, Trichophyton rubrum*, or *Trichophyton mentagrophytes*. They occur on the medial and upper portions of the thighs, and in the pubic area. *Tinea curis* is more commonly seen in males. *Tinea curis* lesions have specific margins with small vessels commonly found. Acute lesions are bright red, and chronic, recurring cases tend to be hyper pigmented.

*Tinea corporis* is known as ringworm of the skin and is more prevalent in climates with higher humidity. *Tinea corporis* usually involves infections by *Trichophyton* or *Microsporum* species. Lesions causes by *Tinea corporis* form on smooth and bear skin areas. These lesions begin as small circular red areas and can become scaling, raised, and pruritic areas.

*Tinea versicolor* is a fungal infection that generally creates cosmetic concerns. Lesions generally occur on seborrheic areas in a confetti-like configuration. This common superficial fungal infection of the stratum corneum is caused by *Ptiyrosporum orbiculare*.

*Candidiasis* or *moniliasis* is caused primarily by *Candida albicans*, and usually occurs in the groin, axilla, interdigital spaces, and under the breasts.

Onychomycosis, or fungal infections of the nail bed or plate, contribute to 40% of all nail disorders. It has been estimated that total United States Medicare costs for treating onychomycosis are in excess of 43 million dollars. Mycotic nail infections are most commonly caused by dermatophytes (*Trichophyton, Microsporum*, and *Epidermophyton* species), yeasts (*Candida* species), and nondermatophyte molds (*Scytalidium, Fusarium, Acremonium, Aspergillus* and *Scopulariopsis*, species). Four major types of mycotic nail infections have been identified: distal subungual onychomycosis, which is the most common type, affecting the plantar surfaces of the hands and feet; white superficial onychomycosis, which affects the toenails; proximal subungual onychomycosis, which is often associated with immunosuppression; and, candidal onychomycosis. These infections vary with respect to the pattern of fungal invasion and causative pathogen. Clinical symptoms of onychomycosis include onycholysis, or separation of the nail from its bed, hyperkeratosis such as calluses or corns, brittleness, color change, and paronychial inflammation, or inflammation due to infection of the skin fold at the nail margin.

Mycotic nail infections do not always resolve spontaneously and may have serious consequences, including limitation of mobility and dexterity, decrease in peripheral circulation in the affected area, and self-consciousness. Onychomycosis can also worsen pre-existing foot problems, such as problems caused in diabetic patients.

Numerous different topical preparations, both prescription and non-prescription, have been used to treat these fungal infections. A significant number of these preparations are sold over-the-counter in drug stores, grocery stores and other retail outlets. On Feb. 26, 1993 the United States Food & Drug Administration identified certain topical antifungal agents that could be generally recommended as safe and effective for non-prescription use, and other agents that could not be recommended. The agents identified as topical non-prescription antifungal agents that are recognized as safe and effective included clioquinal, providone iodine, clortrimazole, tolnaftate, haolprogin, undecylenates, and miconazole nitrate. Those identified as not generally recognized as safe and effective included, alcloza, alum potassium, aluminum sulfate, amyltricreso is, basic fuchsin, benzethomium chloride, benzoic acid, benzoxiquine, boric acid, camphor, candicidin, chlorothymol, coal tar, dichlorophen, menthol, methylparaben, oxyquinoline, oxyquinoline sulfate, phenol, phenolate sodium, phenyl salicylate, propionic acid, propylparaben, resorcinol, salicylic acid, sodium borate, sodium caprylate, sodium propionate, sulfur, tannic acid, thymol, tolindate, triacetin, zinc caprylate, zinc proplonate.

Even the effective agents are not effective in all conditions. In treating patients with immune suppressed disorders such as diabetes, chemotherapy patients, HIV infected patients, and those with chronic infections, fungal infections go untreated or unsuccessfully treated.

In attempting to achieve optimum blood sugar levels in controlling diabetes, infections must be controlled. Infections raise blood sugar levels. Patients with diabetes are generally on a number of medications, including antidiabetic agents, antihypertensives, and lipid lowering drugs. Oral antifungal agents compete with these other medications at the liver for removal from the body. This activity leads to elevated liver enzyme levels. Once liver enzyme levels are elevated, patients have to be taken off of their antifungal and other medications. The same situation holds true with other immunosuppressed patients, including chemotherapy patients and HIV affected patients. Further, drug interactions have to be monitored during treatment with oral antifungal agents.

Accordingly, there is a need to provide an antifungal preparation capable of treating various fungal infections that will effectively work in medically compromised, as well as relatively healthy persons. A topical preparation is the best for this situation, as liver complications are avoided.

SUMMARY OF THE INVENTION

The present invention is a topical antifungal preparation for treatment of fungal infections of the skin and nails. At a minimum, the preparation of the present invention comprises triacetin and an antifungal agent such as tolnaftate, for example. In a preferred form, the preparation comprises triacetin, a fatty acid source such as a fish oil, and an antifungal agent. In a preferred embodiment, the preparation is comprised of 96 to 99% triacetin, 0.5 to 1% cod liver oil and 1 to 3% tolnaftate. Antifungal agents other than tolnaftate may be used. Other agents, such as amino acids, alcohol and garlic oil may also selectively be incorporated into the preparation to aid in its effectiveness. In use, preparation of the present invention is applied topically to the affected area(s) until the infection has been resolved.

DETAILED DESCRIPTION OF THE PREFERRED EMBODIMENTS

Reference will now be made in detail to the present preferred embodiments of the present invention. The present invention is a novel topical antifungal preparation comprised of triacetin in combination with an antifungal agent. In a preferred composition, the preparation is comprised of triacetin, an antifungal agent, and a fish oil or like fatty acid source. In a preferred embodiment, the preparation is comprised of triacetin, cod liver oil and tolnaftate. In one preferred embodiment, this preparation is comprised of 96 to 99% triacetin, 0.5 to 1% cod liver oil, and 0.5 to 3% tolnaftate. It is to be understood that the antifungal agent tolnaftate is only one preferred example of an antifungal agent that can be used. Tolnaftate and triacetin are utilized both because of their antifungal characteristics, as well as the fact that they are safe if improperly or mistakenly ingested by patients.

Other fish oils, such as mandarin oil, shark liver extract, salmon oil, and purified Omega-3 fatty acid fish oils such as OMEGA PURE produced by Omega Protein, Inc. of Reedsville, Va., may be used instead of cod liver oil. However, cod liver oil is beneficial in aiding to heal the skin due to its high levels of vitamins A and D, as well as being relatively inexpensive. Further, other oils, triglicerides, or free fatty acids having similar characteristics to fish oils being high in Omega-3 fatty acids may also be used. Fatty acids aid in antifungal activity. One problem in patients with fungal infections is decreased fatty acid production by the sebaceous glands, due to various causes. By introducing fatty acids to the infected area(s), a more healthy skin environment is restored. Synthetic vitamin A may also be used and works like fish oil from my experiments and trials, due to a deficiency of vitamin A from fungal antimetabolite activity. The yellow color seen in nail infections, or onychomycosis, is caused by the inability of vitamin A precursors being precluded from vitamin A formation and function due to the infection.

Tolnaftate is used topically for the treatment of certain dermatophytoses, such as *Tinea cruris, Tinea corporis, Tinea manuum*, and *Tinea pedis*, which are caused by *Trychophyton rubrum, Trychophyton tonsurans, Microsporum canis, Microsporum audouini*, or *Epidermophyton floccosum*. The exact mode of action of tolnaftate is not known, but the drug has been demonstrated to distort the hyphae and stunt mycelial growth in susceptible fungi. In vitro, tolnaftate is fungistatic or fungicidal to *Microsporum gypseum, Microsporum canis, Microsporum audouini, Microsporum japonicum, Trichophyton rubrum, Trichophyton mentagrophytes, Trichophyton schoenleinii, Trichophyton tonsurans*, and *Epidermophytom floccosum*. Activity of tolnaftate against Aspergillis niger varies from one strain to another.

Triacetin is an odorless, stainless and non-allergenic liquid. Triacetin is an antifungal drug proposed for use in the treatment of superficial fungal infections of the skin, particularly for *Trichophyta, Epidermophyta*, and *Microspora*. The hydrolysis of the ester by myco enzymes releases acetic acid, and any antifungal or antimicotic activity is attributable to the drop in pH. Previous clinical studies by others suggest that the drug is only mildly effective as an antifungal agent when used alone.

In the present preparation, a chemically pure 98 to 99% glyeryl triacetate, formula weight 218.2, increases the activity of the antifungal agent, such as tolnaftate. The increase in activity is accomplished by providing optimal skin exposure by the antifungal agent. Triacetin is used in the cosmetic and food industries for its ability to act as a carrier or vehicle. In this preparation, triacetin acts as a carrier for the antifungal agent, while also increasing the effectiveness of the antifungal agent.

Triacetin also acts to decrease the pH of the application area. It is known that fungus like moist areas and thrive in environments with a normal acidity, pH 6.5 to 7.2. Yeasts die in low pH environments, i.e. pH levels in the range of 4.5 or less, and infectious fungi are adversely affected in low pH environments. Triacetin has a pH of 4.0 when applied to the skin, and effectively lowers the pH of the application area. As triacetin breaks down after application, it produces acetic acid, a weak antifungal agent. Triacetin also acts to lower the moisture content in the application area, which aids in creating an adverse environment for fungal growth. In high concentrations, such is in this preparation, triacetin reduces the secretion of moisture during perspiration, due to an astringent effect, or antihyperhydrosis effect. Triacetin also acts to reduce moisture by bonding with the moisture available in the affected area, reducing the opportunity or availability of the moisture to be utilized by the fungal cells. After application, triacetin also coats the application area, saturating the epidermis and limiting moisture available for fungal growth. Finally, triacetin can also be used for nutritional support whether administered orally, topically or intravenously, to restore healthy, normal skin as is seen with the topical administration of this preparation.

When composed of triacetin in combination with tolnaftate, the present preparation in comprised of 97 to 99.5% triacetin, and 0.5 to 1.0% tolnaftate.

Preferably, the preparation further comprises a fatty acid source, such as cod liver oil. Cod liver oil has long been used as a nutritional supplement to limit infectious disease and for its source of vitamins A and D. One milliliter of cod liver oil contains approximately 850 IU of vitamin A and 85 IU of vitamin D within a rich source of omega-3 fatty acids. No antifungal properties have previously been associated with cod liver oil. Vitamin A in high concentrations may possess some antifungal properties by aiding the body heal itself. Cod liver oil has skin healing and softening properties similar to commercially available vitamins A and D ointments. Vitamin A and fatty acids add synergy in treating fungal infections.

Vitamin A is a fat soluble vitamin that is used in a wide dosage range from 5 to 50,000 I.U. to assist in healing. In post surgical patients, 50,000 international units applied topically to the surgical incision area improved healing time, from my experience and others. Vitamin A is also important for nutritional support. Vitamin D is also a fat soluble vitamin utilized in nutritional support. Vitamin D is not recommended in doses of over 400 milligrams per day. Topical applications with vitamin A and D have been used for years to enhance healing and repair damaged skin.

Numerous fish oils, free fatty acids, triglicerides, or omega-3 fatty acid oils can be used, ideally if they contain natural trace minerals. The oil concentration should be kept low. For example, with cod liver oil, concentrations from 0.5% to 1.0% cod liver oil have been effective. The oil concentration should be kept low due to the increased exposure of the skin to water. Many fungal infections occur with increased perspiration at the site, or in the vicinity of the infection. Use of high concentrations of oil on the skin produces a barrier around the skin, and inhibits the drying necessary for optimal healing and the desirable antifungal environment. Though 0.5% to 1.0% concentrations are effective when using cod liver oil, other more pure sources of fish oil having less barrier characteristics may be used at a concentration up to 3%, within the preparation.

Fungicidal drugs that work in vitro do not always exhibit effective results in vivo. For example, drugs like terbinafine, an antifungal agent with constant presence in nails infected by dermatophytes, needs three months or more of continuous daily intake to show some efficacy. As such, the fungicidal characteristics of terbinafine appear irrelevant in clinical practice. One reason for this is that the status of the fungal cells is quite different in vivo. The fungal cells that are dormant are not responsive to the toxic effects of most antifungal agents in use today. The dormant fungal cells are much less sensitive than hyphae to the action of any current antifungal agent. Fish oil interacts with the triacetin, the selected antifungal agent, and the affected area as follows. Fish oils or omega-3 fatty acid oils and natural trace minerals, change the biological status of the fungal cells from a dormant stage to a growing cell. The growing cells produce hyphae which are susceptible to the toxic effects of effective antifungal agents, including free fatty acids from the fish oil.

The fish oil or omega-3 fatty acid oil also provide nutritional support and healing compounds to the infected skin, aiding in skin regrowth and healing. Additional penetration of the triacetin and selected antifungal agent, into dry, cracked, hardened and/or dead tissue is seen with the addition of omega-3 fatty acids or fish oils.

When combined to create the preparation of the present invention, the fish oil acts as an enhancer for the triacetin and the antifungal agent. The triacetin lowers the pH of the surrounding environment of the fungal infection, as well as reducing the moisture content of this area. Reducing the pH and moisture levels aids in combating the fungal infection. Tolnaftate then works to inhibit the growth and/or kill the fungi infecting the skin and/or nails of the patient. This synergy is needed for therapeutic efficacy.

Other compounds may optionally also be included in the preparation. For example, saturated solutions of n-acetylcysteine improve absorption of tolnaftate into the skin. Other amino acids may be incorporated to aid in absorption, as well as their healing properties. N-acetylcysteine improves penetration of this preparation into the skin and nail at very low concentrations. Topical concentrations from 0.2 to 1.0% are effective. N-acetycysteine has the unique ability to increase glutathione levels in functioning, living skin cells, making them more resistant to damage from toxic substances, and apoptosis or cell death caused by toxic substances. For example cells with high glutathione levels are resistant to chemotherapy. N-acetylcysteine also has positive immune system benefits, including but not limited to improving T. cell function which is deficient in patients prone to fungal infections.

Furthermore, herbal supplements, such as garlic or garlic oil, for example, are incorporated into certain embodiments, for their skin healing and fungistatic and/or fungicidal properties. The garlic oil concentration is limited due to its odor. The mechanism of action of garlic oil is different from antifungal agents on the market today. The proposed mechanism is a direct interaction with the fungus by organic acids and volatile oils, contained within garlic oil, including organosulfur compounds, phytic acid, saponins, amino acids including arginine. Concentrations of 0.08 to 0.1% have been used to increase overall effectiveness of the preparation but use of higher concentrations is limited due to the garlic odor. This can vary with the garlic oil source and growing conditions.

Alcohol, preferably ethyl alcohol, may be used to increase the solubility of other agents of the preparation, including tolnaftate and fish oil within the triacetin solution. Alcohol also aids in combating the growth of the infecting fungi.

In a second preferred embodiment, a preparation is comprised of 95 to 98.8% triacetin, 0.5 to 1.0% cod liver oil, 0.5 to 3.0% tolnaftate, and 0.2 to 1.0% n-acetylcysteine. In another preferred embodiment the preparation is comprised of 94.9 to 98.72% triacetin, 0.5 to 1.0% cod liver oil, 0.5 to 3.0% tolnaftate, 0.2 to 1.0% n-acetylcysteine, and 0.08 to 0.1% garlic oil. In a further preferred embodiment, the preparation is comprised of 79.9 to 93.72% triacetin, 0.5 to 1.0% cod liver oil, 0.5 to 3.0% tolnaftate, 0.2 to 1.0% n-acetylcysteine, 0.08 to 0.1% garlic oil, and 5-15% ethyl alcohol. It should be understood that the components of these embodiments may be selectively included or removed as desired, so long as the preparation includes triacetin, a fish oil, or like fatty acid source and another antifungal agent such as tolnaftate.

In compounding the preparation of the present invention, it is important that the concentration of fish oil or like fatty acid source is not too great. For example, cod liver oil concentrations greater that 1.0% have decreased the effectiveness of this preparation. An increased concentration of fish oil retains the moisture content of the affected area, which aids in fungal growth.

Examples of other antifungal agents that can be combined with fish oils and triacetin to arrive at the preparation include polyenes such as nystatin; imidazoles such as clotrimazole, econazole, ketoconazole, miconazole, solconazole, and oxiconazole; and, allylamines-benzylamines, including naftifine, terbinafine, and butenafine, for example. Other antifungal agents, whether or not presently approved by the U.S. Food & Drug Administration, may be selected and used, once approved and shown effective.

The preparation is applied topically when the infection presents itself, until the infection is removed. The preparation is applied twice daily, until the infection is resolved. For more complicated infections, a longer treatment period is needed. This preparation has shown effective results in diabetic patients, whom had previously been on oral antifungal treatments such as LAMISIL produced by Novartis AG. Clinical examples of the effectiveness of the present invention are set forth below.

Fungal infections complicated by concurrent bacterial infections or non-susceptible fungi, or in patients with systemic diseases such as diabetes, malignancy, and immune suppression such as HIV, or use of certain drugs such as steroids, chemotherapeutic agents, immune suppressants and/or antibiotics, need oral antifungal therapy today. The preparation of the present invention is directed at, and effectively treating fungal infections in patients in these compromised situations, without oral therapies.

Application of this preparation aids in healing the skin itself and treated areas that presented as originally hard, dry, cracked, tissue caused from fungal infections or other conditions, became soft, supple tissue.

CLINICAL EXAMPLES

Patient No. 1—A 32 year old female, suffering from toenail onychomycosis, or a fungal infection of the toenails, and had been treated with oral LAMISIL for three months without resolution of her symptoms. The patient had no pre-existing medical condition or medications. Preparation of the present invention was applied twice daily to the affected area, and no adverse or side effects were seen. At the one and two month check ups, the patient exhibited clearing proximally of the fungus infection on the nail, and regeneration of the nail bed.

Patient No. 2—A 77 year old female, with poor control of her diabetic condition. Patient was unwilling to use oral antifungal therapy. Patient also reported that use of known topical preparations for athletes foot fungal infection were not effective. Preparation of the present invention was applied twice daily to the affected area with total resolution of the fungal infection by the two month check up.

Patient No. 3—A 56 year old diabetic male having a toenail onychomycosis, or fungal infection of the toenails. Preparation of the present invention was applied twice daily, with a clearing of fungal infection proximally, accompanied by regrowth of a clear nail bed and paranycchea devoid. Skin tissue was pink without evidence of dry, cracking skin.

Patient No. 4—A 35 year old male suffering from symptoms consistent with cerebral palsy. Patient is currently on ibuprofin as needed for pain, and 25 mg of ELAVIL by Zeneca, Inc., at bedtime. Patient also has a history of tobacco smoking. At one and two month follow ups, the patient exhibited clearing of the infection, and pink, supple skin tissue.

Although the principles, preferred embodiments and preferred operation of the present invention have been described in detail herein, this is not to be construed as being limited to the particular illustrative forms disclosed. They will thus become apparent to those skilled in the art that various modifications of the preferred embodiments herein can be made without departing from the spirit or scope of the invention as defined by the appended claims.

What is claimed:

1. A topical antifungal preparation comprising:
    A therapeutically effective concentration of triacetin in order to the reduce moisture content of the infected tissue; and,
    An antifungal agent.

2. A topical antifungal preparation as recited in claim 1, wherein said antifungal agent is tolnaftate.

3. A topical antifungal preparation as recited in claim 1, wherein said preparation comprises about 97.0 to 99.5% concentration triacetin, and about 0.5 to 3.0 percent concentration tolnaftate.

4. A topical antifungal preparation as recited in claim 1, further comprising an fatty acid source.

5. A topical antifungal preparation as recited in claim 4, wherein said fatty acid source is selected from the group consisting of fish oils, omega-3 fatty acids, triglicerides, mandarin oil, shark liver extract, salmon oil, and purified omega-3 fatty acid fish oils.

6. A topical antifungal preparation as recited in claim 1, further comprising alcohol.

7. A topical antifungal preparation as recited in claim 1, further comprising amino acids.

8. A topical antifungal preparation as recited in claim 7, wherein said amino acid is n-acetylcystein.

9. A topical antifungal preparation as recited in claim 4, wherein said antifungal agent is tolnaftate.

10. A topical antifungal preparation as recited in claim 9, wherein said fatty acid source is cod liver oil.

11. A topical antifungal preparation as recited in claim 10, wherein said preparation comprises about 96.0 to 99.0% concentration triacetin, about 0.5-3.0 concentration tolnaftate and about 0.5-1.0% concentration cod liver oil.

12. A topical antifungal preparation as recited in claim 1, wherein said antifungal agent is selected from the group consisting of nystatin, clortrimazole, econazole, ketoconazole, miconazole, solconazole, oxiconizole, naftifine, terbinifine, and butenafine.

13. A topical antifungal preparation as recited in claim 4, wherein said antifungal agent is selected from the group consisting of nystatin, clortrimazole, econazole, ketoconazole, miconazole, solconazole, oxiconizole, naftifine, terbinifine, and butenafine.

14. A topical antifungal preparation comprising:
    A therapeutically effective concentration of triacetin in order to the reduce moisture content of the infected tissue;
    An antifungal agent; and
    Synthetic vitamin A.

15. The topical antifungal preparation as recited in claim 14, wherein said antifungal agent is tolnaftate.

16. The topical antifungal preparation as recited in claim 14, wherein said antifungal agent is selected from the group consisting of nystatin, clortrimazole, econazole, ketoconazole, miconazole, solconazole, oxiconizole, naflifine, terbinifine, and butenafine.

17. The topical antifungal preparation as recited in claim 15, wherein said preparation comprises about 96.0-99.0% concentration triacetin, about 0.5-3.0% concentration tolnaftate, and about 0.5-1.0% concentration synthetic vitamin A.

18. The topical antifungal preparation as recited in claim 14, further comprising alcohol.

19. The topical antifungal preparation as recited in claim 14, further comprising amino acids.

20. The topical antifungal preparation as recited in claim 19, wherein said amino acid is n-acetylcysteine.

21. The topical antifungal preparation as recited in claim 10, further comprising n-acetylcysteine.

22. The topical antifungal preparation as recited in claim 21, wherein said preparation comprises about 95.0-98.8% concentration triacetin, about 0.5-1.0% concentration cod liver oil, about 0.5-3.0% concentration tolnaftate, and about 0.2-1.0% concentration n-acetylcysteine.

23. The topical antifungal preparation as recited in claim 22, further comprising garlic oil.

24. The topical antifungal preparation as recited in claim 23, wherein said preparation comprises about 94.9-98.72% concentration triacetin, about 0.5-1.0% concentration cod liver oil, about 0.5-3.0% tolnaftate, about 0.2-1.0% n-acetylcysteine, and about 0.08-1.0% garlic oil.

25. The topical antifungal preparation as recited in claim 23, further comprising ethyl alcohol.

26. The topical antifungal preparation as recited in claim 25, wherein said preparation comprises about 79.9%-93.72% concentration triacetin, about 0.5-1.0% concentration cod liver oil, about 0.5-3.0% concentration tolnaftate, 0.2-1.0% concentration n-acetylcysteine, about 0.08-1.0% concentration garlic oil, and about 5.0-15.0% concentration ethyl alcohol.

* * * * *